United States Patent
Komoda et al.

(10) Patent No.: US 10,107,743 B2
(45) Date of Patent: Oct. 23, 2018

(54) THERMAL INFRARED SENSOR AND GAS MEASURING APPARATUS

(71) Applicant: Murata Manufacturing Co., Ltd., Nagaokakyo-shi, Kyoto-fu (JP)

(72) Inventors: Junya Komoda, Nagaokakyo (JP); Kansho Yamamoto, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 15/386,613

(22) Filed: Dec. 21, 2016

(65) Prior Publication Data

US 2017/0102326 A1    Apr. 13, 2017

Related U.S. Application Data

(63) Continuation of application No. PCT/JP2015/067258, filed on Jun. 16, 2015.

(30) Foreign Application Priority Data

Jul. 4, 2014  (JP) .................................. 2014-138486

(51) Int. Cl.

| G01N 21/35 | (2014.01) |
|---|---|
| G01N 21/3504 | (2014.01) |
| H01L 35/22 | (2006.01) |
| H01L 37/02 | (2006.01) |
| G01N 33/00 | (2006.01) |

(Continued)

(52) U.S. Cl.

CPC ........ *G01N 21/3504* (2013.01); *G01J 5/0831* (2013.01); *G01J 5/0853* (2013.01); *G01J 5/0862* (2013.01); *G01J 5/12* (2013.01); *G01N 21/314* (2013.01); *G01N 33/0009* (2013.01); (Continued)

(58) Field of Classification Search
CPC ...................... G01N 21/3504; G01N 33/0009
See application file for complete search history.

(56) References Cited

U.S. PATENT DOCUMENTS

| 5,721,430 A | 2/1998 | Wong |
|---|---|---|
| 8,047,713 B2 | 11/2011 | Ueno et al. |

(Continued)

FOREIGN PATENT DOCUMENTS

| JP | 2000-503122 A | 3/2000 |
|---|---|---|
| JP | 2009-175124 A | 8/2009 |

(Continued)

OTHER PUBLICATIONS

International Search Report issued for PCT/JP2015/067258, dated Sep. 8, 2015.

(Continued)

Primary Examiner — Marcus Taningco
(74) Attorney, Agent, or Firm — Arent Fox LLP

(57) ABSTRACT

A thermal infrared sensor for gas measurement including a sensing element. The sensing element includes a thermal detection layer that outputs an electric signal based on a temperature change, a light-receiving surface electrode disposed on a light-receiving surface of the thermal detection layer, and a back electrode disposed on the thermal detection layer opposite the light-receiving surface electrode. The light-receiving surface electrode has a periodic structure configured to selectively absorb infrared light having an absorption wavelength of a sample gas.

15 Claims, 14 Drawing Sheets

(51) Int. Cl.
*G01J 5/08* (2006.01)
*G01J 5/12* (2006.01)
*G01N 21/31* (2006.01)
*G01J 3/42* (2006.01)

(52) U.S. Cl.
CPC .............. *H01L 35/22* (2013.01); *H01L 37/02* (2013.01); *G01J 2003/421* (2013.01)

(56) References Cited

U.S. PATENT DOCUMENTS

| 9,335,217 | B2 | 5/2016 | Pisano et al. | |
|---|---|---|---|---|
| 2010/0067016 | A1 | 3/2010 | Ueno et al. | |
| 2010/0276595 | A1* | 11/2010 | Kirby ................... | G02B 5/208 250/339.02 |
| 2011/0180711 | A1* | 7/2011 | Tsuchiya ................. | G01J 5/02 250/338.4 |
| 2013/0256535 | A1* | 10/2013 | Meijer ................. | H01J 47/024 250/340 |
| 2015/0035110 | A1* | 2/2015 | Pisano ................. | G01J 5/0853 257/443 |
| 2016/0365463 | A1* | 12/2016 | Lee ................... | H01L 31/02161 |

FOREIGN PATENT DOCUMENTS

| JP | 2012-220419 | A | 11/2012 |
|---|---|---|---|
| JP | 2013-113692 | A | 6/2013 |

OTHER PUBLICATIONS

Kansho Yamamoto et al.; "Pyroelectric aluminum nitride micro electromechanical systems infrared sensor with wavelength-selective infrared absorber"; Applied Physics Letters 104, 111111, (2014).

Ogawa, Shinpei et al.; "Wavelength Selective Uncooled Infrared Sensor by Plasmonic Absorber"; Mitsubishi Denki Giho, Jun. 25, 2013, vol. 87, No. 6, pp. 353-356.

Written Opinion of the International Searching Authority issued for International Application No. PCT/JP2015/067258, dated Sep. 8, 2015.

* cited by examiner

THERMAL INFRARED SENSOR AND GAS MEASURING APPARATUS

CROSS REFERENCE TO RELATED APPLICATIONS

The present application is a continuation of International application No. PCT/JP2015/067258, filed Jun. 16, 2015, which claims priority to Japanese Patent Application No. 2014-138486, filed Jul. 4, 2014, the entire contents of each of which are incorporated herein by reference.

FIELD OF THE INVENTION

The present invention relates to a thermal infrared sensor and a gas measuring apparatus. More particularly, the present invention relates to a thermal infrared sensor for gas measurement and a gas measuring apparatus including the thermal infrared sensor.

BACKGROUND OF THE INVENTION

Many gases have their characteristic infrared absorption wavelengths in the infrared spectrum region. One known apparatus for measuring a particular gas utilizing this characteristic is a non-dispersive infrared (NDIR) gas measuring apparatus. Such a gas measuring apparatus is composed mainly of an infrared light source, a gas cell, a band-pass optical filter, and an infrared sensor.

An infrared sensor described in Patent Document 1 (Japanese Unexamined Patent Application Publication (Translation of PCT Application) No. 2000-503122) includes a detector that includes a narrow band-pass optical filter that transmits infrared light having an absorption wavelength of a target gas, and two detectors that include band-pass optical filters that transmit two reference wavelengths different from the absorption wavelength of the target gas. The concentration of a sample gas can be measured by processing the output signals of these three detectors.

Patent Document 2 (Japanese Unexamined Patent Application Publication No. 2013-113692) and Patent Document 3 (Japanese Unexamined Patent Application Publication No. 2012-220419) disclose a thermal infrared sensor for use in NDIR gas measuring apparatuses. A thermal infrared sensor disclosed in Patent Document 2 is a pyroelectric infrared sensor composed of a pyroelectric material layer formed of an aluminum nitride piezoelectric material and a pair of electrodes disposed on each side of the pyroelectric material layer. Patent Document 3 discloses that a pyroelectric infrared sensor contains a ceramic material, such as $PbTiO_3$, $Pb(Zr,Ti)O_3$ (PZT), or $Pb(Zr,Ti)O_3$—$Pb(Mn,Nb)O_3$ (PZT-PMN), a single crystal material, such as $LiTaO_3$ or $LiNbO_3$, or a polymeric material, such as $PVF_2$, as a material of a pyroelectric material layer.

Patent Document 1: Japanese Unexamined Patent Application Publication (Translation of PCT Application) No. 2000-503122

Patent Document 2: Japanese Unexamined Patent Application Publication No. 2013-113692

Patent Document 3: Japanese Unexamined Patent Application Publication No. 2012-220419

SUMMARY OF THE INVENTION

In such a thermal infrared sensor, infrared light is simply used as a heat source, and a sensor (a thermal detection layer, such as a pyroelectric material layer) itself has a low wavelength dependence. Thus, in order to selectively measure a particular sample gas (for example, $CO_2$), the sensor must be configured to only receive infrared light having a wavelength corresponding to an absorption wavelength of the sample gas through a special band-pass optical filter.

Such a band-pass optical filter increases the size of the apparatus, and band-pass optical filters for use in NDIR gas measuring apparatuses are generally expensive, thus increasing component costs. In particular, gas measuring apparatuses including a referential sensing element as disclosed in Patent Document 1 require a plurality of band-pass optical filters (for example, three band-pass optical filters, including one for detection and two for reference), which increase the size of the apparatuses and component costs.

In view of the problems described above, it is an object of the present invention to provide a thermal infrared sensor for gas measurement that can reduce the size of apparatuses and can reduce component costs, and a gas measuring apparatus including the thermal infrared sensor.

A thermal infrared sensor for gas measurement according to an embodiment of the present invention includes a sensing element that has a thermal detection layer for outputting a temperature change as an electric signal; a light-receiving surface electrode disposed on a light-receiving surface of the thermal detection layer; and a back electrode disposed on the thermal detection layer opposite the light-receiving surface electrode. The light-receiving surface electrode has a periodic structure for selectively absorbing infrared light having an absorption wavelength of a sample gas.

Preferably, the periodic structure has a plurality of cavities arranged at regular intervals.

In the thermal infrared sensor, the sample gas is preferably $CO_2$ gas and has an absorption wavelength in the range of 4.2 to 4.4 µm.

Preferably, the plurality of cavities of the periodic structure are arranged at intervals in the range of 4.1 to 4.3 µm.

In the preferred thermal infrared sensor, the light-receiving surface electrode has a cavity ratio in the range of 50% to 90%.

The thermal detection layer is preferably a pyroelectric material layer.

Preferably, the pyroelectric material layer is composed mainly of AlN.

The pyroelectric material layer also preferably has a thickness in the range of 100 to 350 nm.

The light-receiving surface electrode is preferably formed of a material composed mainly of at least one selected from the group consisting of Au, Ag, Pt, Al, Mo, W, and Ru.

The back electrode is preferably formed of a material composed mainly of at least one selected from the group consisting of Mo, Al, Ru, and Ti.

Another aspect of the present invention is a thermal infrared sensor for gas measurement including a first sensing element and a second sensing element. The first sensing element includes a first thermal detection layer for outputting a temperature change as an electric signal; a first light-receiving surface electrode disposed on a light-receiving surface of the first thermal detection layer; and a first back electrode disposed on the first thermal detection layer opposite the first light-receiving surface electrode. The second sensing element includes a second thermal detection layer for outputting a temperature change as an electric signal; a second light-receiving surface electrode disposed on a light-receiving surface of the second thermal detection layer; and a second back electrode disposed on the second thermal detection layer opposite the second light-receiving surface electrode. The first light-receiving surface electrode preferably has a first periodic structure for selectively absorbing infrared light having an absorption wavelength of a sample gas, and the second light-receiving surface electrode preferably has a second periodic structure for selectively absorbing infrared light having a reference wavelength different from the absorption wavelength of the sample gas.

The reference wavelength preferably ranges from 3.5 to 4.15 µm or 4.5 to 5.0 µm.

Preferably, the first sensing element and the second sensing element are integrally formed.

A gas measuring apparatus according to an aspect of the present invention includes the thermal infrared sensor noted above; an infrared light source; and a gas cell.

The present invention can provide a thermal infrared sensor for gas measurement that can reduce the size of apparatuses and can reduce component costs, and a gas measuring apparatus including the thermal infrared sensor.

DETAILED DESCRIPTION OF THE PREFERRED EMBODIMENTS

First Embodiment

Figure 1:
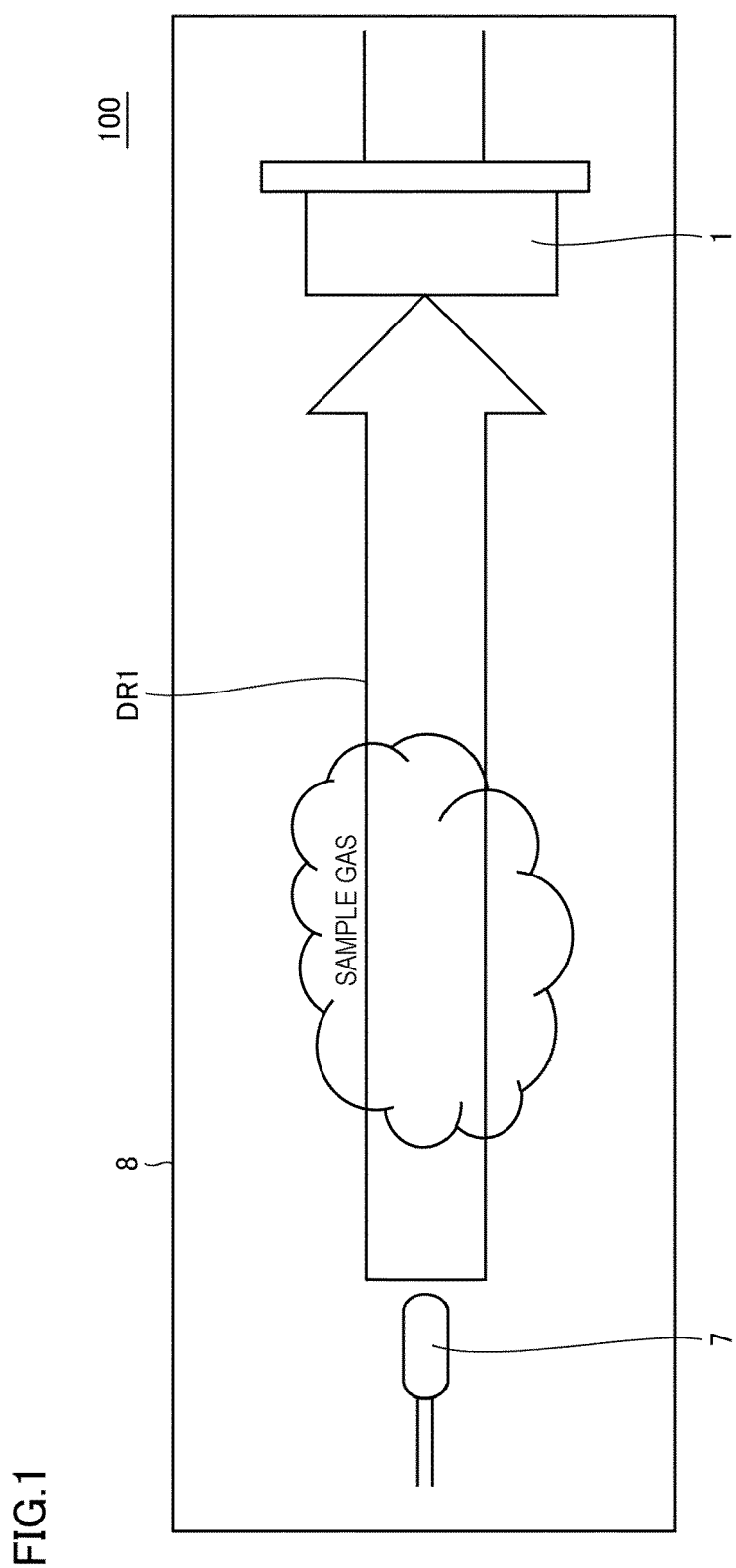
FIG. 1 is a schematic cross-sectional view of a gas measuring apparatus including a thermal infrared sensor according to a first embodiment.

A thermal infrared sensor and a gas measuring apparatus including the thermal infrared sensor according to an embodiment will be described below with reference to the accompanying drawings. Like reference numerals denote like parts or equivalents thereof throughout the figures.

(Gas Measuring Apparatus)

FIG. 1 is a schematic cross-sectional view of a gas measuring apparatus including a thermal infrared sensor according to the present embodiment. First, a gas measuring apparatus 100 including a thermal infrared sensor will be outlined below with reference to FIG. 1.

As illustrated in FIG. 1, the gas measuring apparatus 100 according to the present embodiment includes a thermal infrared sensor 1 for detecting infrared light, an infrared light source 7 for emitting infrared light, and a gas cell (sample cell) 8. The gas measuring apparatus 100 measures the concentration or the like of a sample gas between the infrared light source 7 and the thermal infrared sensor 1 in the gas cell 8 as a function of the absorbance or the like of the sample gas.

For example, the gas cell 8 has an internal space through which a sample gas flows. More specifically, one end of the gas cell 8 (near the infrared light source 7) is coupled to a sample gas inlet pipe (not shown), and the other end of the gas cell 8 (near the thermal infrared sensor 1) is coupled to a sample gas outlet pipe (not shown). A sample gas introduced into the internal space of the gas cell 8 through the sample gas inlet pipe is discharged from the sample gas outlet pipe.

The infrared light source 7 emits infrared light. For example, the infrared light source 7 is a filament lamp or LED lamp that emits broadband infrared light including desired infrared light. Part of infrared light emitted from the infrared light source 7 is absorbed by a sample gas in accordance with the absorption characteristics of the sample gas. Infrared light emitted from the infrared light source 7 travels mainly in the optical axis direction DR1 (in the direction of the arrow in the figure) and reaches the thermal infrared sensor 1.

The thermal infrared sensor 1 is electrically connected to a signal-processing circuit board (not shown) and sends an output signal based on the amount of detected infrared light to the signal-processing circuit board. The signal-processing circuit board calculates the concentration or the like of the sample gas from the output signal.

Figure 16:
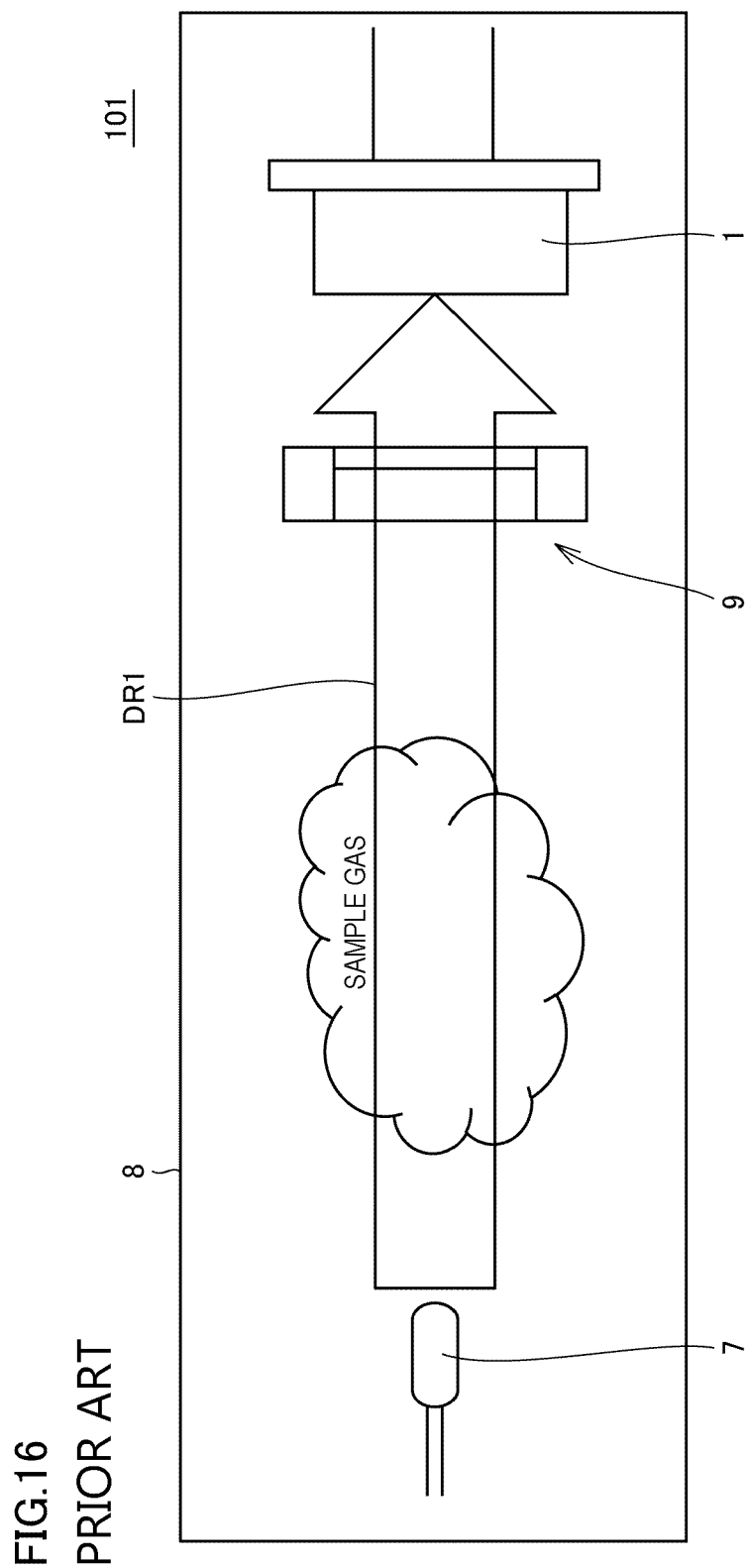
FIG. 16 is a schematic cross-sectional view of a known gas measuring apparatus including a thermal infrared sensor.

Unlike a known gas measuring apparatus 101 (see FIG. 16), the gas measuring apparatus according to the present embodiment includes no band-pass optical filter 9. This is because, as described later, a periodic structure of a light-receiving surface electrode in a sensing element used in the thermal infrared sensor 1 functions as a band-pass optical filter.

(Thermal Infrared Sensor)

The thermal infrared sensor 1 according to the present embodiment will be described in detail below.

Figure 2A:
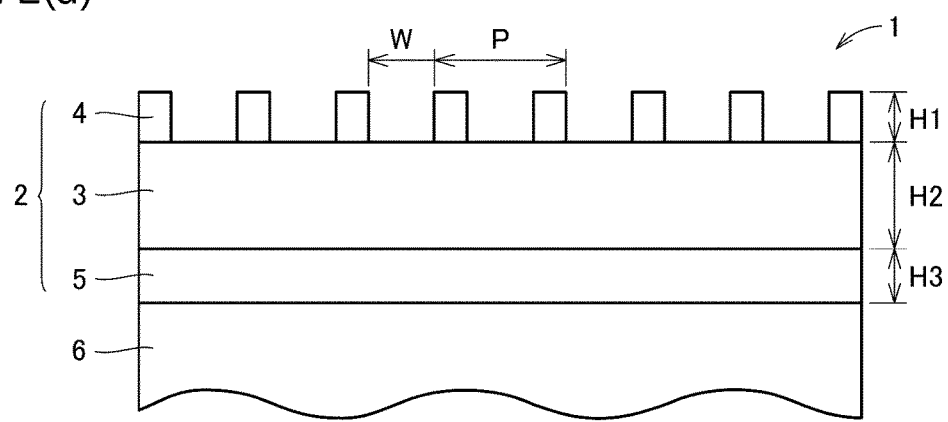
FIG. 2(a) is a schematic cross-sectional view of the thermal infrared sensor according to the first embodiment.

Thermal (non-cooling) infrared sensors are sensors that receive light in an infrared region (infrared light), convert the light into heat, convert the heat into an electric signal, and detects the electric signal. Referring to FIG. 2(a), the thermal infrared sensor 1 according to the present embodiment is a MEMS sensor that includes a sensing element 2 on a support layer 6, and is used for gas measurement.

The sensing element 2 includes a thermal detection layer 3 for outputting a temperature change as an electric signal (such as a pyroelectric material layer), a light-receiving surface electrode 4 disposed on a light-receiving surface of the thermal detection layer, and a back electrode 5 disposed on the thermal detection layer 3 opposite the light-receiving surface electrode 4.

For example, the sensing element 2 is a pyroelectric element that utilizes the pyroelectric effect (a sensing element that includes a pyroelectric material layer as a thermal detection layer), a thermoelectric element that utilizes the thermoelectric effect (a sensing element that includes a thermopile as a thermal detection layer), or a sensing element that includes a bolometer as a thermal detection layer, the bolometer utilizing the effect of an electrical resistance change due to a temperature change. Among these, the sensing element 2 is preferably a pyroelectric element in terms of sensitivity and the ease of manufacture. A pyroelectric element can efficiently detect electric charges generated in a pyroelectric material layer serving as the thermal detection layer 3 with the light-receiving surface electrode 4 and the back electrode 5 and therefore has higher sensitivity than thermoelectric elements. Furthermore, a light-receiving surface electrode having a periodic structure can be more easily formed on a pyroelectric material layer in pyroelectric elements than on a thermocouple or resistor in thermoelectric elements.

Examples of the material of a pyroelectric material layer for use in pyroelectric elements include ceramic materials, such as $PbTiO_3$, $Pb(Zr,Ti)O_3$ (PZT), and $Pb(Zr,Ti)O_3$—$Pb(Mn,Nb)O_3$ (PZT-PMN), single crystal materials, such as $LiTaO_3$ and $LiNbO_3$, and polymeric materials, such as $PVF_2$.

The light-receiving surface electrode 4 has a periodic structure for selectively absorbing infrared light having an absorption wavelength of a sample gas. This enables the sensing element 2 to exclusively detect infrared light in a desired wavelength band.

The periodic structure is preferably a periodic structure or a quasi-periodic structure. Periodic structures refer to structures that have spatial symmetry, such as translational symmetry, and quasi-periodic structures refer to structures that have no translational symmetry but have an ordered arrangement. Periodic structures are divided into one-dimensional periodic structures, two-dimensional periodic structures, and three-dimensional periodic structures, depending on the dimensions of symmetry. Among these periodic structures, two-dimensional periodic structures are preferably used.

For example, the periodic structure of the light-receiving surface electrode 4 is composed of a plurality of cavities arranged in at least one direction at regular intervals on a main surface of the light-receiving surface electrode 4. For example, such a periodic structure is a two-dimensional periodic structure in which a plurality of cavities 4a are arranged in a square grid at regular intervals when viewed from the top (see FIG. 2(*b*)).

Although the plurality of cavities 4a arranged at regular intervals are circular when viewed from the top in FIG. 2(*b*), the plurality of cavities 4a may be rectangular or hexagonal when viewed from the top. The plurality of cavities 4a may be entirely arranged at regular intervals, or part of the cavities 4a may be arranged at irregular intervals, provided that infrared light having an absorption wavelength of a sample gas can be selectively absorbed.

When the thermal infrared sensor 1 is irradiated with infrared light from the infrared light source 7, infrared light in a specific wavelength range depending on various parameters of such a periodic structure of the light-receiving surface electrode 4 (such as the size and pitch of the cavities 4a, and the thicknesses of the light-receiving surface electrode 4 and the thermal detection layer 3) can cause resonance in the sensing element 2. The energy of infrared light that causes resonance is converted into heat in the sensing element 2, the heat is absorbed by the thermal detection layer 3 and is converted into an electric signal, and the electric signal is output from (detected by) the light-receiving surface electrode 4 and the back electrode 5.

The periodic structure of the light-receiving surface electrode 4 and the material and thickness of the thermal detection layer 3 can be designed to cause resonance at an absorption wavelength of a sample gas, and the light-receiving surface electrode 4 can selectively absorb infrared light having an absorption wavelength of the sample gas and convert the infrared light into heat, so that the thermal detection layer 3 can absorb the heat.

In thermal infrared sensors, infrared light is simply used as a heat source, and sensors (elements) themselves have a low wavelength dependence. Thus, in order to selectively measure a particular sample gas (for example, $CO_2$), a known sensor must be configured to only receive infrared light having a wavelength corresponding to an absorption wavelength of the sample gas through a special band-pass optical filter 9 (see FIG. 16). In the present invention, a periodic structure of the light-receiving surface electrode 4 functions as a band-pass optical filter. This obviates the need for a special expensive band-pass optical filter, can reduce the size of the apparatus, and can reduce component costs.

The material of the light-receiving surface electrode is preferably a material (metallic material) composed mainly of at least one selected from the group consisting of Au, Ag, Pt, Al, Mo, W, and Ru, more preferably a material composed mainly of Al. These materials are resistant to oxidation. Thus, the light-receiving surface electrode is resistant to oxidation and can be used without a protective film. These materials can reflect infrared light and can advantageously reduce absorption of infrared light having a wavelength other than the absorption wavelength of $CO_2$. The term "main component", as used herein, refers to a component present in the greatest amount in the material. The ratio of a main component to the total material is preferably 80% or more by weight, more preferably 90% or more by weight. The light-receiving surface electrode may be a multilayer body composed of a plurality of metal layers, such as a Ti or NiCr close contact layer.

The material of the back electrode is preferably a material (metallic material) composed mainly of at least one selected from the group consisting of Mo, Al, Ru, and Ti. These materials can reflect infrared light and can advantageously reduce absorption of infrared light having a wavelength other than the absorption wavelength of $CO_2$. These materials function as an underlying metal film of a thermal detection layer, such as a high-crystallinity AlN film (pyroelectric material layer) and advantageously facilitate the formation of a thermal detection layer.

In order to increase electrical resistance between the light-receiving surface electrode and the back electrode and to enhance the sensitivity of the thermal infrared sensor (sensing element), the sensing element may include an insulating layer between the thermal detection layer and the back electrode.

A thermal infrared sensor according to the present embodiment is a micro electro mechanical systems (MEMS) sensor, in which necessary components are integrated on a substrate, and can advantageously reduce the size of apparatuses.

(Method for Manufacturing Thermal Infrared Sensor)

A method for manufacturing the thermal infrared sensor (pyroelectric infrared sensor) according to the present embodiment will be described below.

First, an AlN layer (support layer), a Mo layer (back electrode), and an AlN layer (pyroelectric material layer) are formed on a silicon wafer (substrate) in this order by a sputtering method. Both faces of the silicon wafer are polished. These layers have a thickness of 1 μm, 0.2 μm, and 0.23 μm, respectively.

Figure 2B:
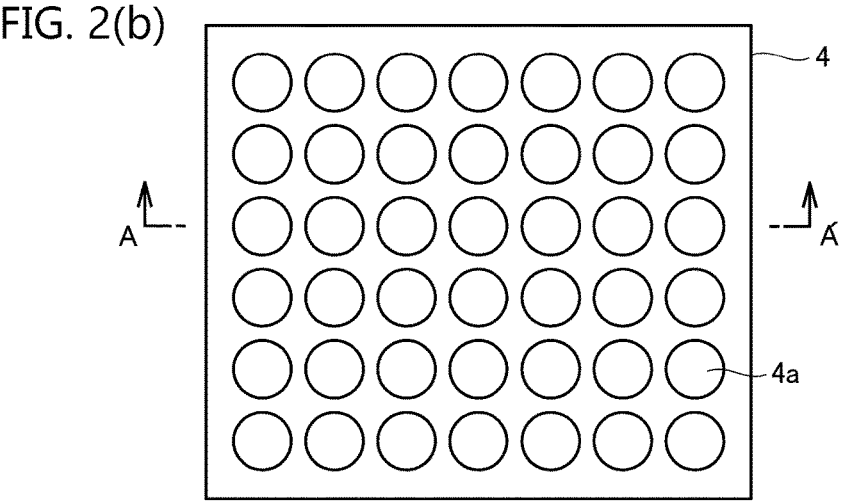
FIG. 2(b) is a schematic top view of the thermal infrared sensor according to the first embodiment.

A multilayer body (light-receiving surface electrode) composed of a Ti layer and an Al layer is formed by a lift-off method. More specifically, the multilayer body is formed as described below. First, a resist pattern is formed on the substrate on which the AlN layer (support layer), the Mo layer (back electrode), and the AlN layer (pyroelectric material layer) are formed, and then a Ti layer and an Al layer are formed in this order from the substrate side by a sputtering method. These layers have a thickness of 3 nm and 0.1 μm, respectively. The resist pattern is removed together with part of the Ti layer and the Al layer formed on the resist pattern, thus forming a multilayer body (light-receiving surface electrode) composed of the Ti layer and the Al layer. Since the resist pattern has a desired shape, the multilayer body (light-receiving surface electrode) composed of the Ti layer and the Al layer has a hole array shape (a plurality of cavities are arranged in a square grid, as illustrated in FIGS. 2(a) and 2(b)). The pyroelectric material layer (AlN layer) is then partly removed by wet etching to partly expose the back electrode.

A side of the substrate (Si) opposite the back electrode is subjected to deep reactive ion etching (DRIE) to partly remove the substrate, thereby partly exposing a surface of the support layer (AlN layer) adjacent to the substrate. The support layer functions as an etch-stop layer.

The following design parameters for the hole array shape of the light-receiving surface electrode formed by the dry etching method are optimized so that a target gas is selectively absorbed. This enables the light-receiving surface electrode to selectively absorb infrared light having an absorption wavelength of a target gas and obviates the need for an expensive optical filter.

The design parameters include parameters with respect to the periodic structure of the light-receiving surface electrode, such as the pitch (the intervals of arrangement) and size (diameter) of the cavities, the thickness of the light-receiving surface electrode, and the thickness of the pyroelectric material layer (thermal detection layer). These design parameters can be optimized to design the periodic structure of the light-receiving surface electrode such that resonance occurs at an absorption wavelength of a sample gas.

(Simulation 1)

The infrared absorption characteristics of a sensing element (sensing element for $CO_2$ measurement) were determined in a simulation using a finite-difference time-domain (FDTD) method and using the thermal infrared sensor (pyroelectric infrared sensor) illustrated in FIGS. 2(a) and 2(b) as an analytical model.

Table 1 lists the parameter settings for the analytical model of the sensing element. In Table 1, P, W, H1, H2, and H3 correspond to the signs in FIGS. 2(a) and 2(b). The pitch, cavity diameter, and cavity ratio are parameters for cavities in a light-receiving surface electrode. The cavity ratio is the ratio of cavity diameter to pitch (W/P).

TABLE 1

| Parameters | Settings |
| --- | --- |
| Pitch P (μm) | 4.1 |
| Cavity diameter W (μm) | 3.1 |
| Cavity ratio W/P (%) | 75.6 |
| Thickness H1 of light-receiving surface electrode (μm) | 0.1 |

TABLE 1-continued

| Parameters | Settings |
| --- | --- |
| Thickness H2 of pyroelectric material layer (μm) | 0.23 |
| Thickness H3 of back electrode (μm) | 0.2 |

Figure 3:
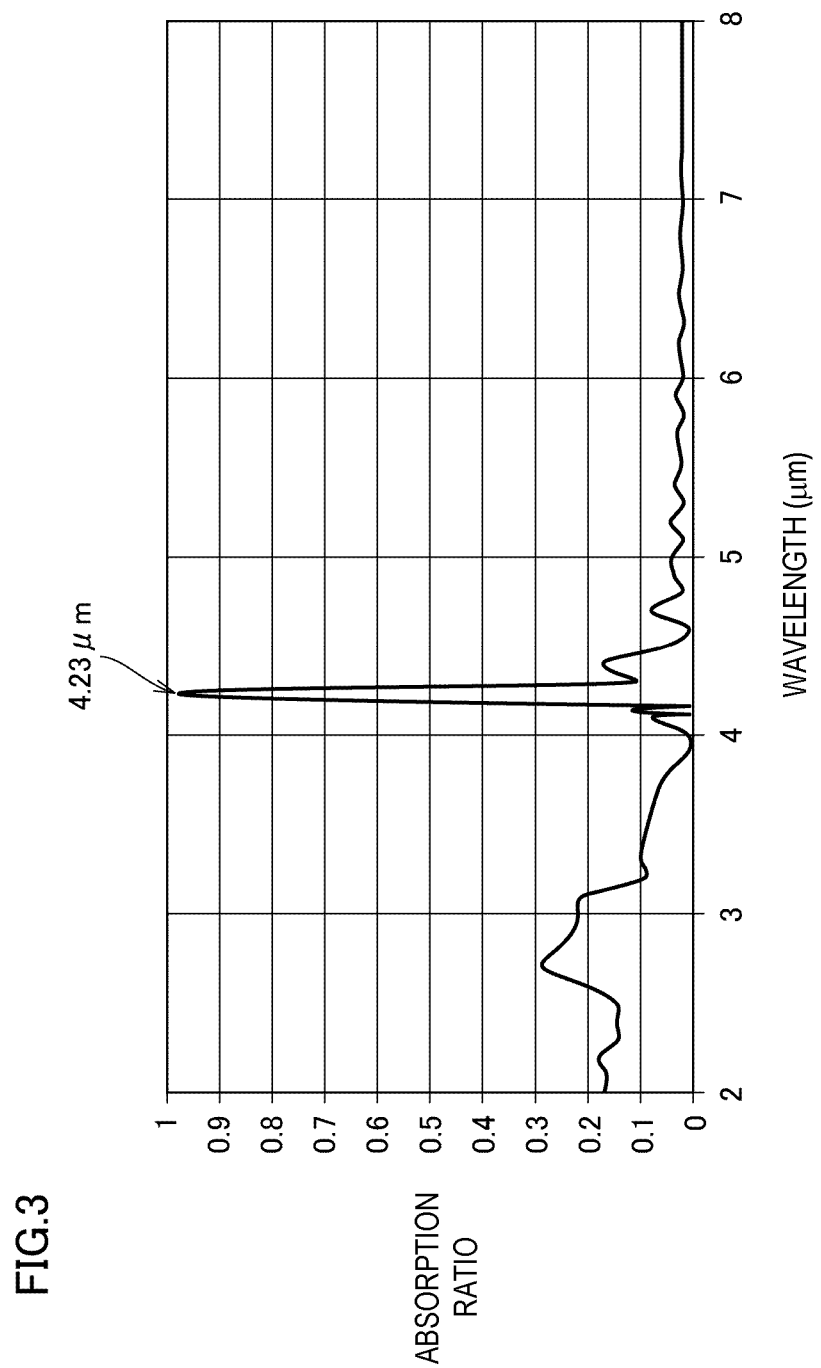
FIG. 3 is a graph of the infrared absorption characteristics of a sensing element obtained in Simulation 1.

FIG. 3 shows the infrared absorption characteristics (absorption spectrum) of the sensing element obtained by the simulation. FIG. 3 shows that the absorptivity of infrared light is as high as 97% at a wavelength of 4.23 μm and has a sharp peak characteristic.

(Simulation 2)

Figure 4:
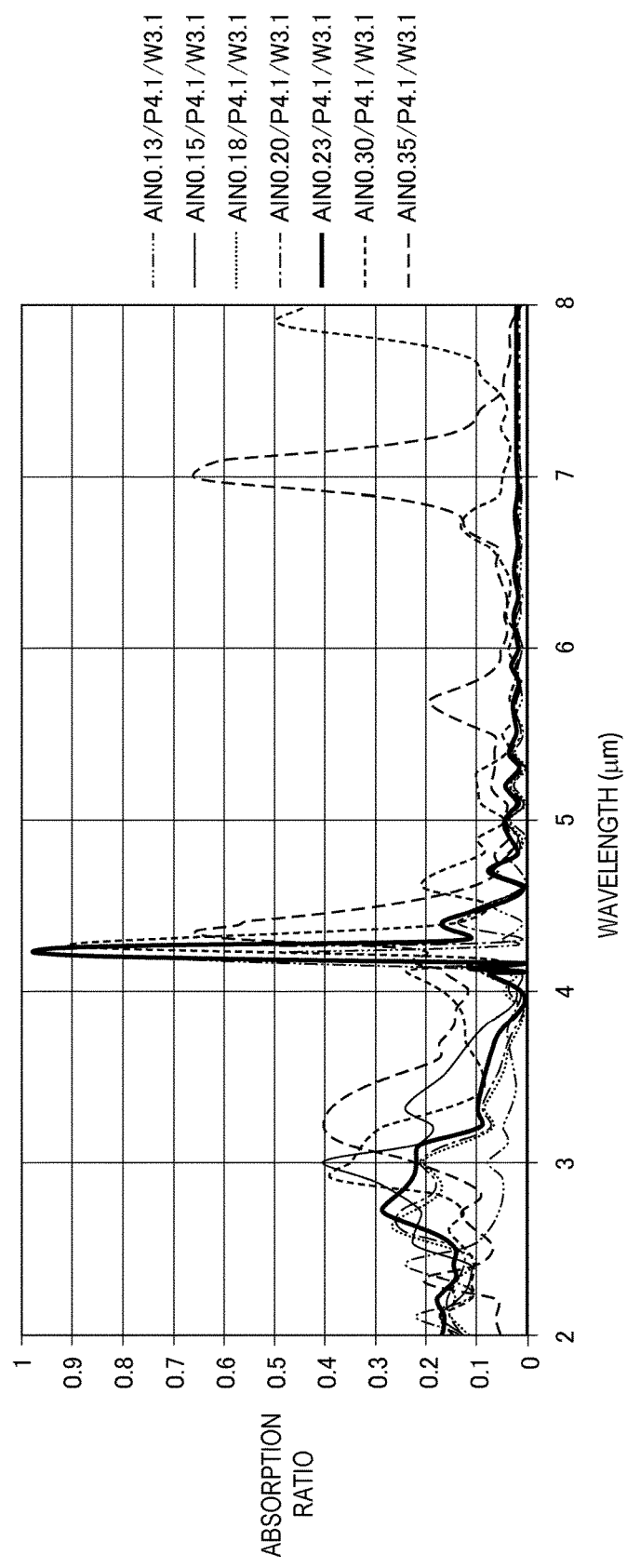
FIG. 4 is a graph of absorption characteristics obtained in Simulation 2.

In the same manner as in Simulation 1, the absorption characteristics were determined by only changing the thickness of the pyroelectric material layer (AlN layer) (the values on the right of AlN in FIG. 4, unit: μm). FIG. 4 shows the absorption characteristics.

Figure 5:
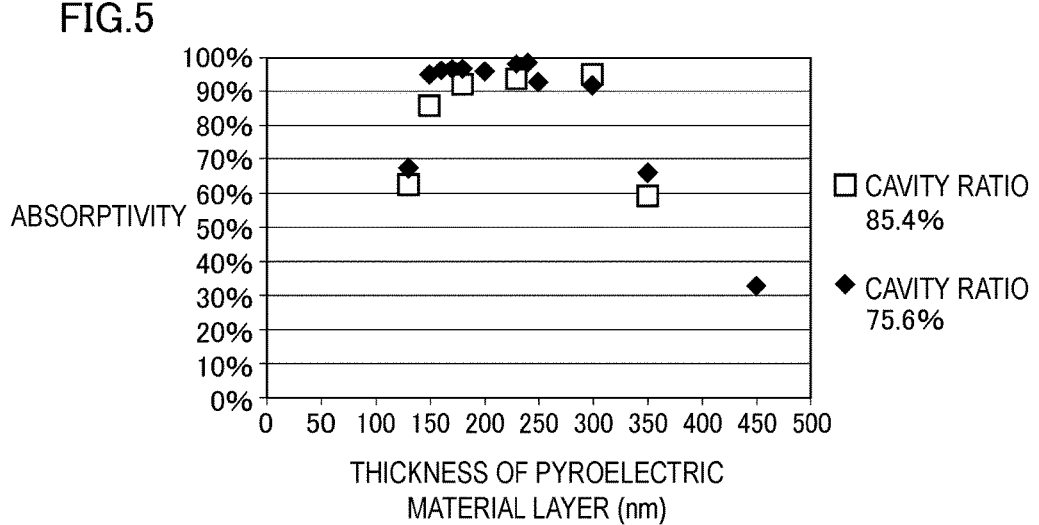
FIG. 5 is a graph of the relationship between the thickness of a pyroelectric material layer and absorptivity obtained in Simulation 2.

The relationship between the thickness of the pyroelectric material layer and absorptivity at an infrared absorption wavelength of $CO_2$ (4.2 μm to 4.4 μm) was determined in the same manner as in the simulation described above. The cavity ratio of the light-receiving surface electrode was 75.6% (P: 4.1 μm, W: 3.1 μm) or 85.4% (P: 4.1 W: 3.5 μm). FIG. 5 shows the results.

FIGS. 4 and 5 show that a sharp filter characteristic can be obtained when the pyroelectric material layer has a thickness in the range of 100 to 350 nm. This tendency is also observed when the cavity ratio of the light-receiving surface electrode is changed.

(Absorption Spectrum of $CO_2$)

Figure 6:
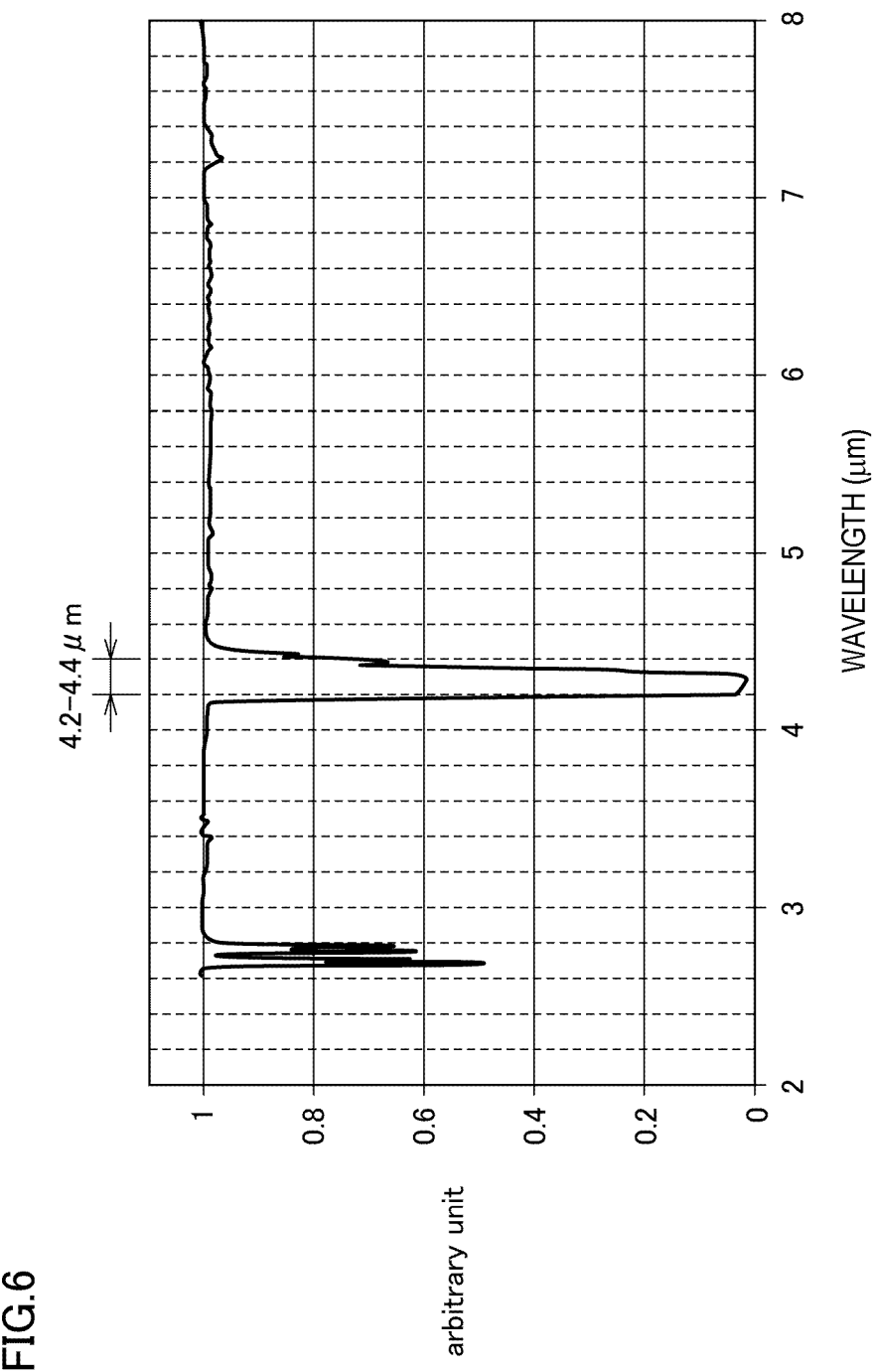
FIG. 6 is the absorption spectrum of $CO_2$.

FIG. 6 shows the absorption spectrum of $CO_2$ available from "National Institute of Standards and Technology", U.S.A. FIG. 6 shows that the absorption wavelength of $CO_2$ ranges from 4.2 to 4.4 μm.

(Simulation 3)

Figure 7:
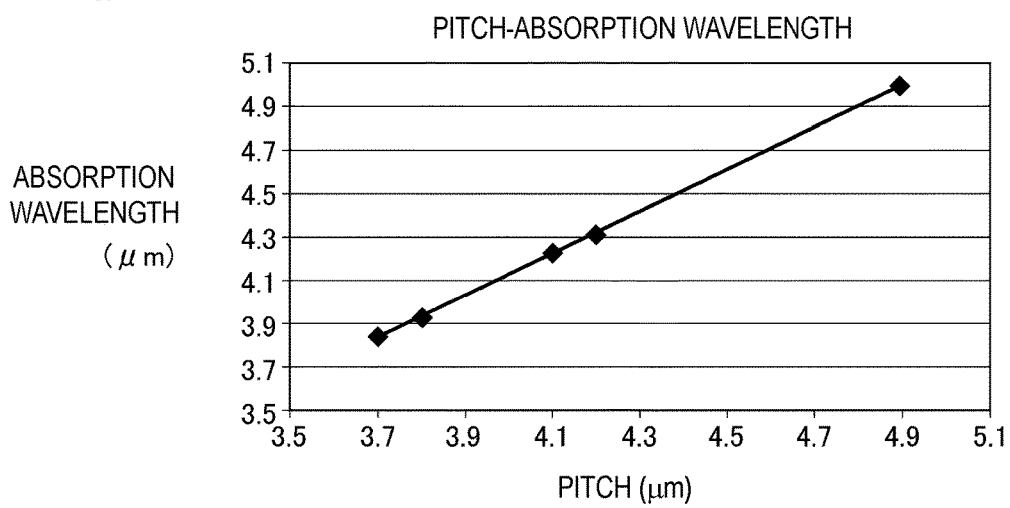
FIG. 7 is a graph of the relationship between the pitch of cavities in a light-receiving surface electrode and absorption wavelength obtained in Simulation 3.

In the same manner as in Simulation 1, the absorption wavelength was determined by changing the pitch of cavities in the light-receiving surface electrode. FIG. 7 shows the relationship between the pitch of cavities in the light-receiving surface electrode and the absorption wavelength obtained by this simulation.

FIG. 7 shows that infrared light having a $CO_2$ absorption wavelength (4.2 to 4.4 μm) is selectively absorbed when the pitch of cavities in the light-receiving surface electrode ranges from 4.1 to 4.3 μm. FIG. 7 also shows that the absorption wavelength depends on the pitch.

(Simulation 4)

Figure 8:
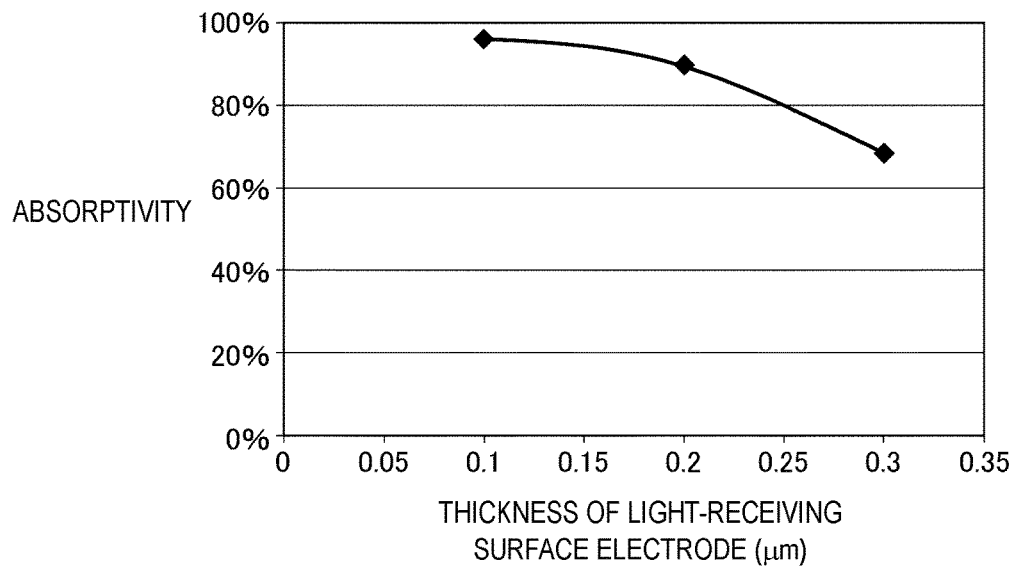
FIG. 8 is a graph of the relationship between the thickness of a light-receiving surface electrode and absorptivity obtained in Simulation 4.

In the same manner as in Simulation 1, absorptivity was determined for different thicknesses of the light-receiving surface electrode. FIG. 8 shows the relationship between the thickness of the light-receiving surface electrode and absorptivity obtained by this simulation.

Although the thickness of the light-receiving surface electrode is 0.1 μm in the parameters listed in Table 1, FIG. 8 shows that high absorptivity can be achieved when the light-receiving surface electrode has a thickness of 0.3 μm or less.

The thickness of the back electrode may be, but is not limited to, 0.1 μm or more, at which infrared transmission through the back electrode is almost negligible.

(Simulation 5)

Figure 9:
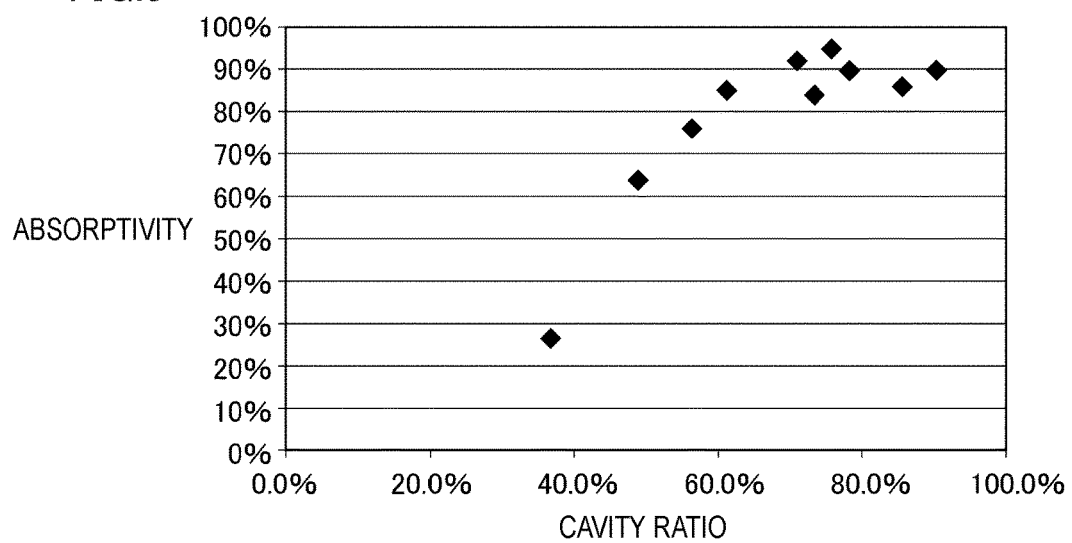
FIG. 9 is a graph of the relationship between the cavity ratio and absorptivity obtained in Simulation 5.

In the same manner as in Simulation 1, absorptivity was determined for different cavity ratios. FIG. 9 shows the relationship between the cavity ratio and absorptivity obtained by the simulation.

FIG. 9 shows that absorptivity can be 60% or more at a cavity ratio of 50% or more and can be 80% or more at a cavity ratio of 60% or more. The cavity ratio is preferably 90% or less due to a limited manufacturing process. With a cavity ratio in such a range, a sharp absorption characteristic can be achieved for infrared light having a wavelength in the range of 4.2 to 4.4 μm corresponding to the $CO_2$ absorption wavelength.

Second Embodiment

A thermal infrared sensor according to the present embodiment is a thermal infrared sensor (MEMS sensor) that includes a first sensing element (sensing element for measurement) and a second sensing element (referential sensing element).

The first sensing element includes a first thermal detection layer for outputting a temperature change as an electric signal, a first light-receiving surface electrode disposed on a light-receiving surface of the first thermal detection layer, and a first back electrode disposed on the first thermal detection layer opposite the first light-receiving surface electrode. The first light-receiving surface electrode has a first periodic structure for selectively absorbing infrared light having an absorption wavelength of a sample gas.

The second sensing element includes a second thermal detection layer for outputting a temperature change as an electric signal, a second light-receiving surface electrode disposed on a light-receiving surface of the second thermal detection layer, and a second back electrode disposed on the second thermal detection layer opposite the second light-receiving surface electrode. The second light-receiving surface electrode has a second periodic structure for selectively absorbing infrared light having a reference wavelength different from the absorption wavelength of the sample gas.

The second sensing element is configured not to absorb infrared light in an absorption band of a sample gas to be detected. The absorption wavelength of the second sensing element ranges from 3.5 to 4.15 μm or 4.5 to 5.0 μm. A wavelength in the range of 3.5 to 4.15 μm and 4.5 to 5.0 μm is preferred. As disclosed in a document "Sekigaisen Kougaku (Infrared Light Engineering)" (Haruyoshi Kuno, The Institute of Electronics, Information and Communication Engineers), p. 55, this wavelength range corresponds to the so-called "atmospheric window", which has high light transmittance with a little atmospheric influence, and a wavelength in this range is a suitable referential wavelength.

It is generally known that variations in the amount of infrared light emitted from the infrared light source 7 or variations in ambient temperature cause a deviation in the output of the thermal infrared sensor 1. In the present embodiment, the thermal infrared sensor 1 includes a first sensing element 21 (sensing element for measurement) and a second sensing element 22 (referential sensing element), and output from the first sensing element 21 can be corrected on the basis of the difference between output from the second sensing element 22 receiving infrared light and output from the second sensing element 22 not receiving infrared light. This correction can enhance the reliability of values measured with the thermal infrared sensor 1.

In the same manner as in the first embodiment, the present embodiment does not require a band-pass optical filter for measurement (for an absorption wavelength of a sample gas) and a referential band-pass optical filter (for a reference wavelength). This can reduce the size of the apparatus and reduce component costs.

(Simulation 6)

The infrared absorption characteristics were determined by the same simulation as described above with the same analytical model as the first embodiment except that the parameter settings for the analytical model were changed as listed in Table 2. This analytical model was designed as an example of a second sensing element (referential sensing element) for selectively absorbing light having a wavelength in the range of 3.5 to 4.15 μm and 4.5 to 5.0 μm.

TABLE 2

| Parameters | Settings |
|---|---|
| Pitch P (μm) | 3.8 |
| Cavity diameter W (μm) | 3.0 |
| Cavity ratio W/P (%) | 78.9 |
| Thickness H1 of light-receiving surface electrode (μm) | 0.1 |
| Thickness H2 of pyroelectric material layer (μm) | 0.23 |
| Thickness H3 of back electrode (μm) | 0.2 |

Figure 10:
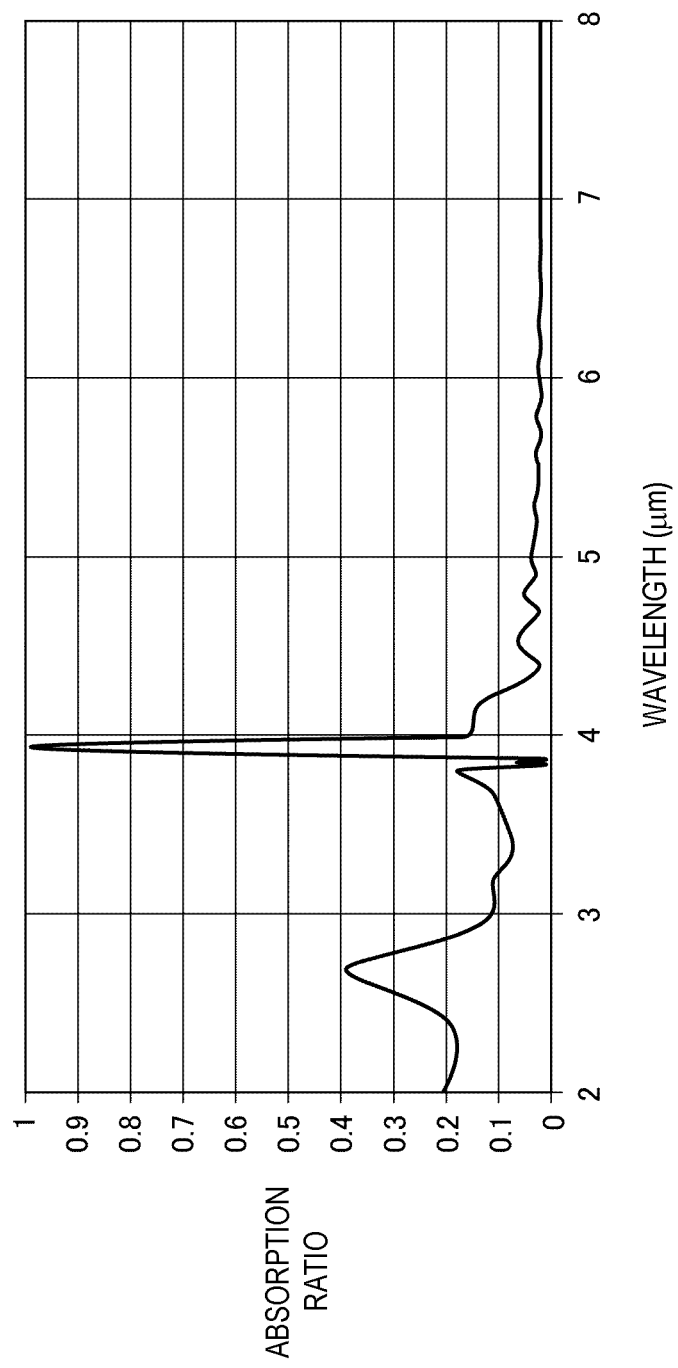
FIG. 10 is a graph of the absorption characteristics obtained in Simulation 6.

FIG. 10 shows the infrared absorption characteristics obtained by the simulation. FIG. 10 shows that the analytical model having the design parameters listed in Table 2 absorbs light having a wavelength of approximately 3.9 μm.

(Simulation 7)

Figure 11:
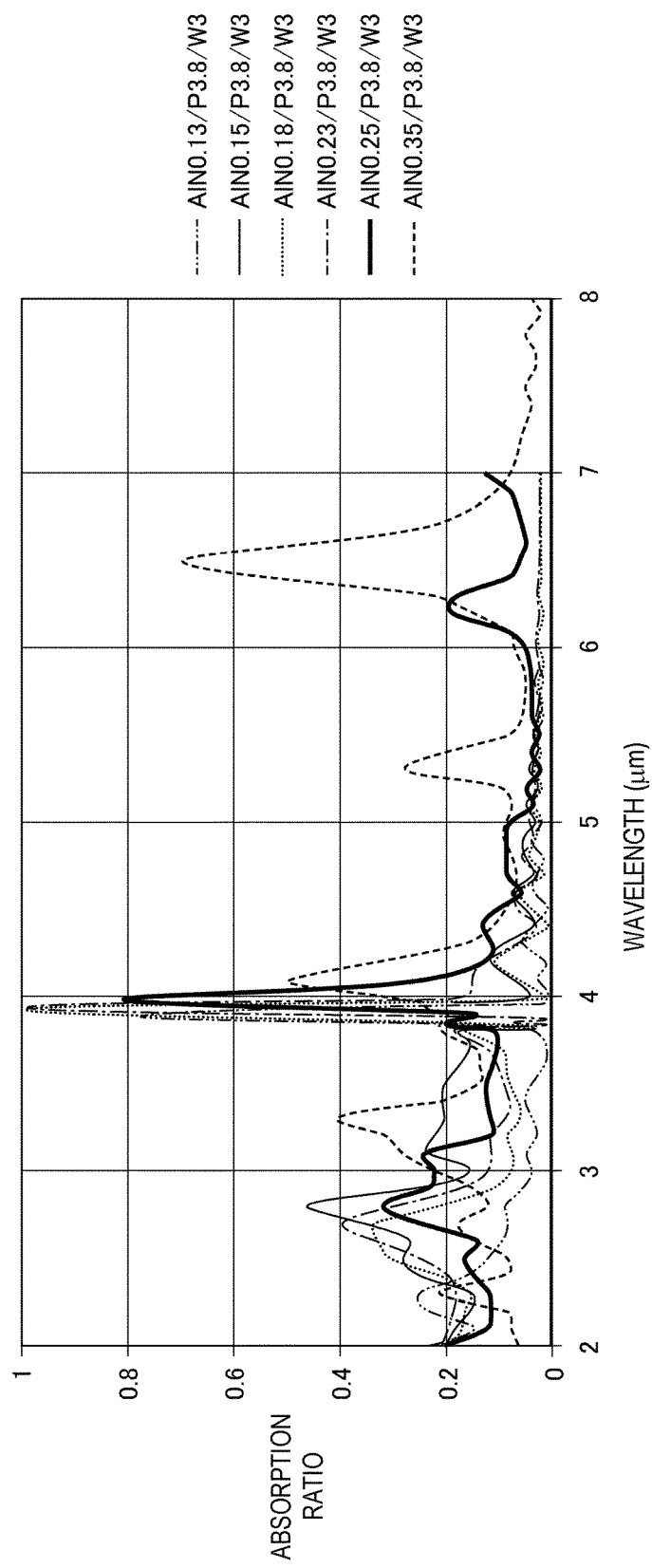
FIG. 11 is a graph of absorption characteristics obtained in Simulation 7.

In the same manner as in Simulation 6, the absorption characteristics were determined by only changing the thickness of the pyroelectric material layer (AlN layer) (the values on the right of AlN in FIG. 11, unit: μm). FIG. 11 shows the absorption characteristics.

Figure 12:
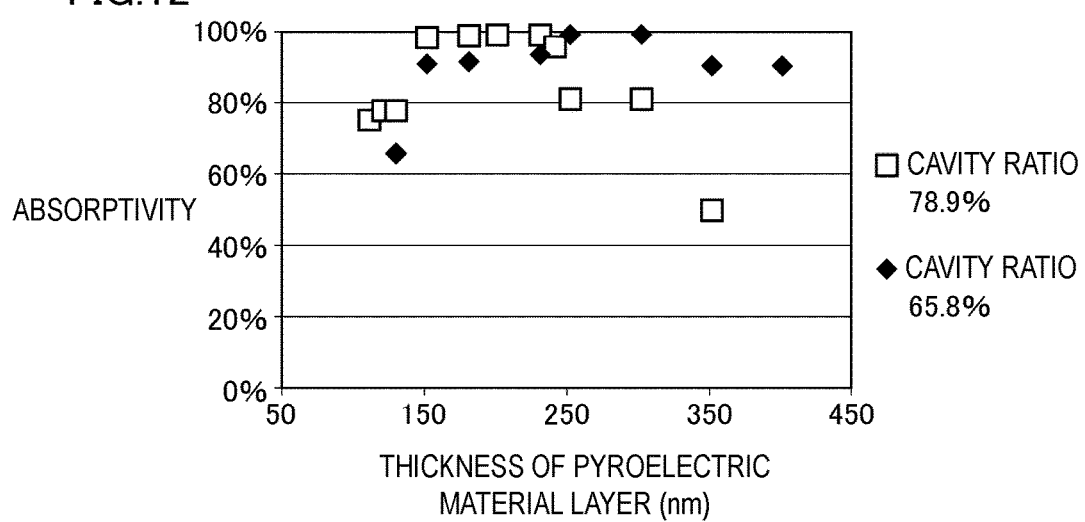
FIG. 12 is a graph of the relationship between the thickness of a pyroelectric material layer and absorptivity obtained in Simulation 7.

The relationship between the thickness of the pyroelectric material layer and the absorptivity of an absorption peak at a wavelength of approximately 3.9 μm was determined in the same manner as in the simulation described above. The cavity ratio of the light-receiving surface electrode was 65.8% (P: 3.8 μm, W: 2.5 μm) or 78.9% (P: 3.8 μm, W: 3.0 μm). FIG. 12 shows the results.

FIGS. 11 and 12 show that a sharp absorption characteristic can be achieved at a wavelength of 3.9 μm when the pyroelectric material layer has a thickness in the range of 100 to 350 nm, and the cavity ratio ranges from 60% to 90%.

(Simulation 8)

The infrared absorption characteristics of the sensing element were determined in the same manner as in Simulation 6 except that the parameter settings R1 to R7 for the analytical model were changed as listed in Table 3 such that the pitch and diameter of cavities in the light-receiving surface electrode were suitable for the reference wavelength range.

TABLE 3

| Parameters | Settings | | | | | | |
|---|---|---|---|---|---|---|---|
| | R1 | R2 | R3 | R4 | R5 | R6 | R7 |
| Pitch P (μm) | 3.4 | 3.7 | 3.8 | 4.0 | 4.5 | 4.7 | 4.9 |
| Cavity diameter W (μm) | 2.5 | 3.0 | 3.0 | 3.0 | 3.5 | 3.7 | 3.7 |
| Cavity ratio W/P (%) | 73.5 | 81.1 | 78.9 | 75.0 | 77.8 | 78.7 | 75.5 |
| Thickness H1 of light-receiving surface electrode (μm) | 0.1 | 0.1 | 0.1 | 0.1 | 0.1 | 0.1 | 0.1 |
| Thickness H2 of pyroelectric material layer (μm) | 0.23 | 0.23 | 0.23 | 0.23 | 0.23 | 0.23 | 0.23 |
| Thickness H3 of back electrode (μm) | 0.2 | 0.2 | 0.2 | 0.2 | 0.2 | 0.2 | 0.2 |

Figure 13:
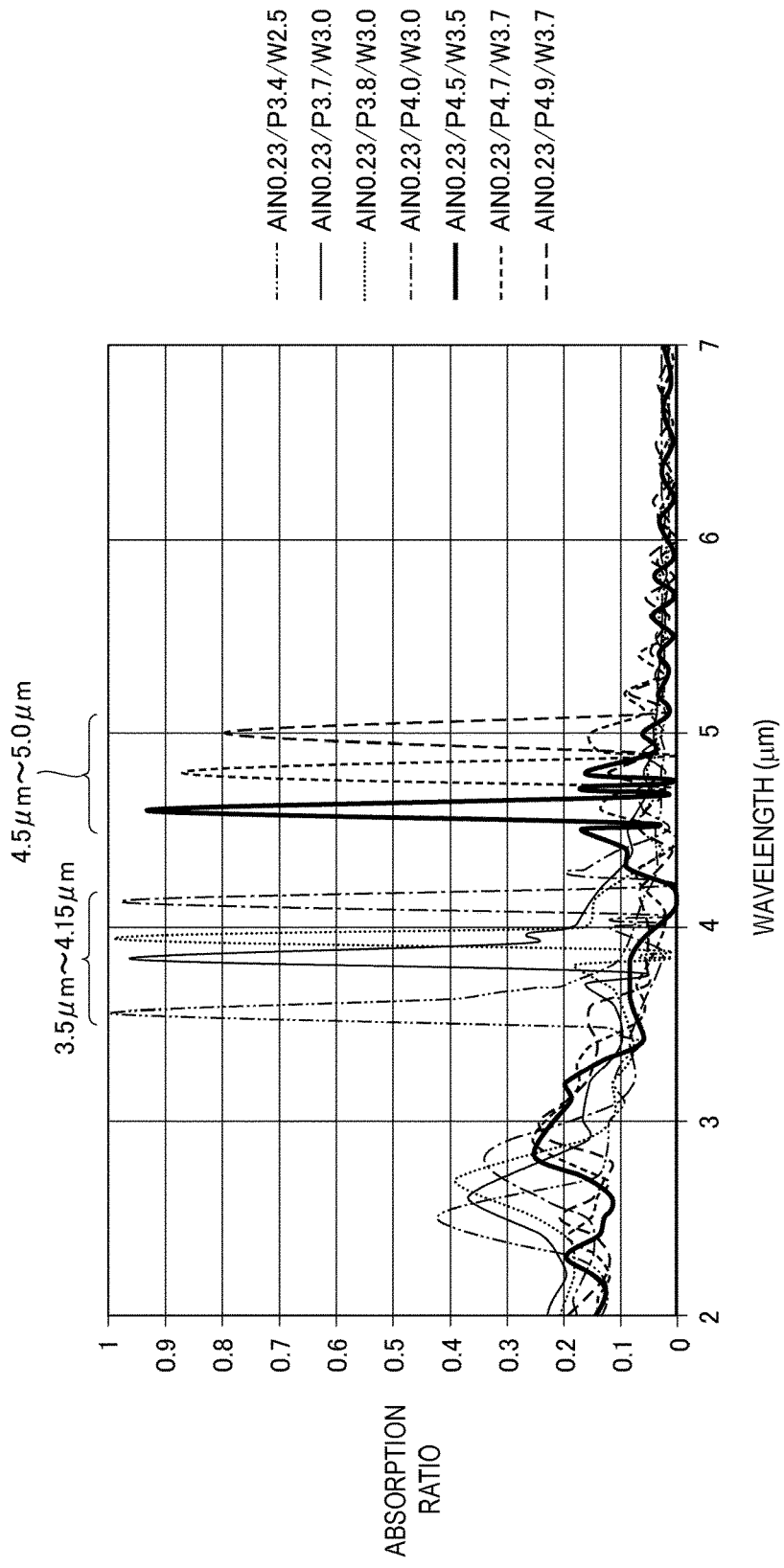
FIG. 13 is a graph of absorption characteristics obtained in Simulation 8.

FIG. 13 shows the infrared absorption characteristics obtained by the simulation. The results in FIG. 13 show that a periodic structure having an absorption wavelength in the reference wavelength range can be formed by setting the parameters, such as the pitch and diameter of cavities in the light-receiving surface electrode, as listed in Table 3.

Figure 14:
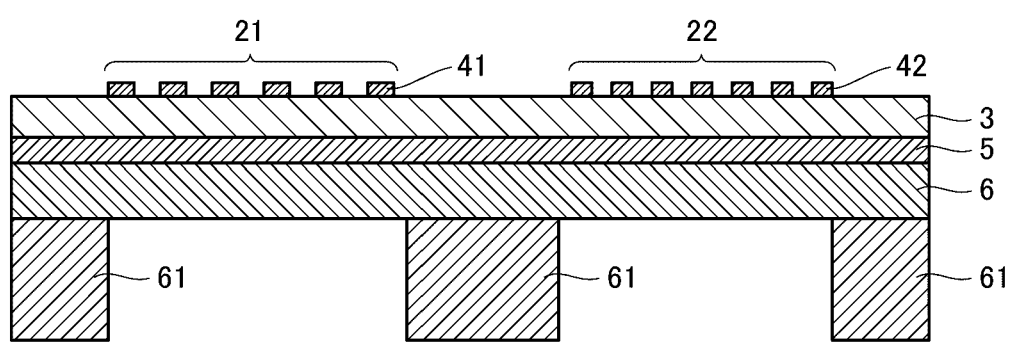
FIG. 14 is a schematic view of a structure of a thermal infrared sensor according to a second embodiment.
Figure 15:
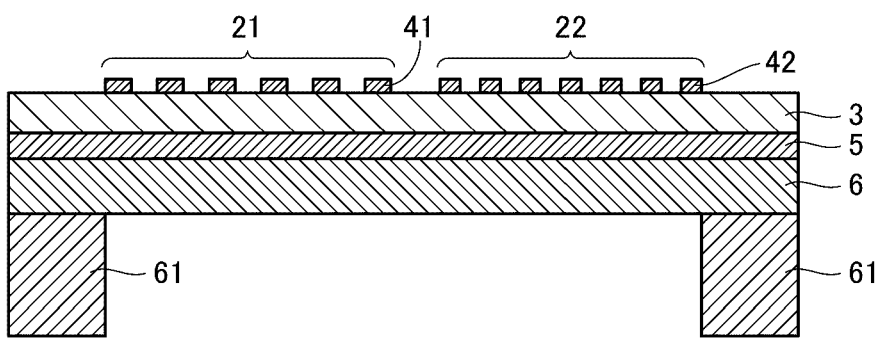
FIG. 15 is a schematic view of another structure of the thermal infrared sensor according to the second embodiment.

The first sensing element (sensing element for measurement) and the second sensing element (referential sensing element) may not be separated chips and may be integrally formed on one substrate, as illustrated in FIG. 14 or 15.

More specifically, in a thermal infrared sensor illustrated in FIG. 14, the first sensing element 21 includes a first thermal detection layer for outputting a temperature change as an electric signal (part of the thermal detection layer 3), a first light-receiving surface electrode 41 disposed on a light-receiving surface of the first thermal detection layer, and a first back electrode (part of the back electrode 5) disposed on the first thermal detection layer opposite the first light-receiving surface electrode 41. The second sensing element 22 includes a second thermal detection layer for outputting a temperature change as an electric signal (part of the thermal detection layer 3), a second light-receiving surface electrode 42 disposed on a light-receiving surface of the second thermal detection layer, and a second back electrode (part of the back electrode 5) disposed on the second thermal detection layer opposite the second light-receiving surface electrode 42. These first sensing element 21 and second sensing element 22 are disposed on the support layer 6. Although the first thermal detection layer and the second thermal detection layer as well as the first back electrode and the second back electrode are integrally formed in the thermal infrared sensor illustrated in FIG. 14, the first light-receiving surface electrode 41 is separated from the second light-receiving surface electrode 42. Reference numeral 61 indicates a substrate having a through-hole below the first thermal detection layer and the second thermal detection layer. The through-holes decrease the heat capacities of the first thermal detection layer and the second thermal detection layer and thereby increase the sensitivity of the sensor. Furthermore, the two through-holes thermally isolate the first thermal detection layer from the second thermal detection layer, thus preventing sensor outputs from influencing each other.

In the thermal infrared sensor illustrated in FIG. 15, although the first sensing element 21 and the second sensing element 22 have the structure illustrated in FIG. 14, the first light-receiving surface electrode 41 and the second light-receiving surface electrode 42 are continuously formed, and the first sensing element 21 and the second sensing element 22 are integrally formed over one through-hole in the substrate 61 disposed on the support layer 6.

As illustrated in FIG. 15, integral formation of the first sensing element and the second sensing element on the substrate can further reduce the size of the apparatus and further reduce component costs.

It is to be understood that the embodiments disclosed herein are illustrated by way of example and not by way of limitation in all respects. The scope of the present invention is defined by the appended claims rather than by the description preceding them. All modifications that fall within the scope of the claims and the equivalents thereof are therefore intended to be embraced by the claims.

REFERENCE SIGNS LIST thermal infrared sensor, 2 sensing element, 21 first sensing element, 22 second sensing element, 3 thermal detection layer, 4 light-receiving surface electrode, 41 first light-receiving surface electrode, 42 second light-receiving surface electrode, 4a cavities, 5 back electrode, support layer, 61 substrate, 7 infrared light source, 8 gas cell, 9 band-pass optical filter, 100, 101 gas measuring apparatus

The invention claimed is:

1. A thermal infrared sensor comprising:
a light-receiving surface electrode having a periodic structure configured to selectively absorb infrared light having an absorption wavelength of a sample gas;
a back electrode; and
a thermal detection layer between the light-receiving surface electrode and the back electrode, the thermal detection layer constructed to output an electric signal based on a temperature change, wherein
the periodic structure has a plurality of cavities arranged at regular intervals,
the sample gas is a $CO_2$ gas and has an absorption wavelength in a range of 4.2 to 4.4 µm, and
the light-receiving surface electrode has a cavity ratio in a range of 50% to 90%.

2. The thermal infrared sensor according to claim 1, wherein the plurality of cavities of the periodic structure are arranged at intervals in a range of 4.1 to 4.3 µm.

3. The thermal infrared sensor according to claim 1, wherein the thermal detection layer is a pyroelectric material layer.

4. The thermal infrared sensor according to claim 3, wherein a main component of the pyroelectric material layer is AlN.

5. The thermal infrared sensor according to claim 4, wherein the pyroelectric material layer has a thickness in a range of 100 to 350 nm.

6. The thermal infrared sensor according to claim 3, wherein the pyroelectric material layer has a thickness in a range of 100 to 350 nm.

7. The thermal infrared sensor according to claim 1, wherein a main component of the light-receiving surface electrode is at least one material selected from the group consisting of Au, Ag, Pt, Al, Mo, W, and Ru.

8. The thermal infrared sensor according to claim 1, wherein a main component of the back electrode is at least one material selected from the group consisting of Mo, Al, Ru, and Ti.

9. A gas measuring apparatus comprising:
the thermal infrared sensor according to claim 1;
an infrared light source that provides the infrared light; and
a gas cell that provides the sample gas.

10. A thermal infrared sensor for gas measurement comprising:
a first sensing element comprising:
a first light-receiving surface electrode having a first periodic structure configured to selectively absorb first infrared light having an absorption wavelength of a sample gas;
a first back electrode; and
a first thermal detection layer between the first light-receiving surface electrode and the first back electrode, the first thermal detection layer constructed to output a first electric signal based on a first temperature change; and
a second sensing element comprising:
a second light-receiving surface electrode having a second periodic structure configured to selectively absorb second infrared light having a reference wavelength different from the absorption wavelength of the sample gas;

a second back electrode; and a second thermal detection layer between the second light-receiving surface electrode and the second back electrode, the second thermal detection layer constructed to output a second electric signal based on a second temperature change, wherein the periodic structure has a plurality of cavities arranged at regular intervals, the sample gas is a $CO_2$ gas and has an absorption wavelength in a range of 4.2 to 4.4 μm, and the light-receiving surface electrode has a cavity ratio in a range of 50% to 90%.

11. The thermal infrared sensor according to claim 10, wherein the reference wavelength ranges from 3.5 to 4.15 μm.

12. The thermal infrared sensor according to claim 10, wherein the reference wavelength ranges from 4.5 to 5.0 μm.

13. The thermal infrared sensor according to claim 10, wherein the first sensing element and the second sensing element are integral.

14. The thermal infrared sensor according to claim 10, wherein the first thermal detection layer and the second thermal detection layer integral.

15. A gas measuring apparatus comprising:

the thermal infrared sensor according to claim 10;

an infrared light source that provides the first infrared light and the second infrared light; and a gas cell that provides the sample gas.

* * * * *